(12) United States Patent
Park et al.

(10) Patent No.: US 7,115,674 B2
(45) Date of Patent: Oct. 3, 2006

(54) DENTAL SELF-CURING RESIN CEMENT COMPOSITIONS

(75) Inventors: Kwang Soo Park, Seoul (KR); Sang Soon Park, Seoul (KR); Kyu Hyun Baek, Goyang-si (KR); Min Sung Kim, Seoul (KR); Dong Keun Han, Seoul (KR)

(73) Assignee: Dentkist, Inc., Seoul (KR)

( * ) Notice: Subject to any disclaimer, the term of this patent is extended or adjusted under 35 U.S.C. 154(b) by 395 days.

(21) Appl. No.: 10/699,117

(22) Filed: Oct. 31, 2003

(65) Prior Publication Data

US 2005/0049326 A1 Mar. 3, 2005

(30) Foreign Application Priority Data

Aug. 29, 2003 (KR) ............... 10-2003-0060180

(51) Int. Cl.
*A61K 6/083* (2006.01)
*C08K 3/22* (2006.01)

(52) U.S. Cl. ............... 523/116; 523/120; 524/431; 433/228.1

(58) Field of Classification Search ............... 523/116, 523/120; 433/228.1
See application file for complete search history.

(56) References Cited

U.S. PATENT DOCUMENTS

| 4,427,799 | A | * | 1/1984 | Orlowski et al. | 523/116 |
| RE32,073 | E | * | 1/1986 | Randklev | 523/117 |
| 5,122,061 | A | * | 6/1992 | Wakumoto et al. | 433/228.1 |
| 5,228,907 | A | * | 7/1993 | Eppinger et al. | 106/35 |
| 5,444,104 | A | * | 8/1995 | Waknine | 522/24 |

* cited by examiner

*Primary Examiner*—Tae H. Yoon
(74) *Attorney, Agent, or Firm*—Jones Day

(57) ABSTRACT

The present invention refers to dental self-curing resin compositions having enhanced mechanical and physical properties. In particular, the present invention relates to dental self-curing resin compositions consisting of (i) a Paste A composition containing the multifunctional prepolymer mixture of 2,2-bis-[4-(2-hydroxy-3-methacryloxypropoxy)phenyl]propane ("Bis-GMA") and multifunctional prepolymer formed by substituting hydrogen atoms in hydroxyl group with methacrylate groups in the Bis-GMA molecules, and further containing a diluent, an adhesive monomer, a polymerization initiator, a polymerization inhibitor, a light stabilizer, an antioxidant, an inorganic pigment and an inorganic filler; and ii) a Paste B composition containing the same prepolymer mixture in the Paste A composition, and further containing a diluent, an adhesive monomer, a reductant, a polymerization inhibitor, a light stabilizer, an antioxidant, an inorganic pigment and an inorganic filler. The composition according to the present invention has better physical and mechanical properties than that of conventional compositions and is an ointment-ointment system able to be conveniently used.

9 Claims, No Drawings

DENTAL SELF-CURING RESIN CEMENT COMPOSITIONS

FIELD OF THE INVENTION

The present invention relates to dental self-curing resin cement compositions having enhanced mechanical and physical properties and biocompatibility. Specifically, the present invention relates to dental self-curing resin cement compositions consisting of (i) a Paste A composition containing the multifunctional prepolymer mixture of 2,2-bis-[4-(2-hydroxy-3-methacryloxypropoxy)phenyl]propane ("Bis-GMA") and multifunctional prepolymers formed by substituting hydrogen atoms in hydroxyl group with methacrylate groups in Bis-GMA, and further containing a diluent, an adhesive monomer, a polymerization initiator, a polymerization inhibitor, a light stabilizer, an antioxidant, an inorganic pigment and an inorganic filler; and ii) a Paste B composition containing the same prepolymer mixture in the Paste A composition, and further containing a diluent, an adhesive monomer, a reductant, a polymerization inhibitor, a light stabilizer, an antioxidant, an inorganic pigment and an inorganic filler.

BACKGROUND OF THE INVENTION

A self-curing resin cement, which is filled in a small quantity with methyl methacrylate as a component, was introduced in the 1950s. Initially, however, it was rarely used due to its high polymerization shrinkage and prelimbic leak, tendency to stimulate dental pulp, poor handling properties, etc. Thereafter, the enamel etching technique and the direct-filling composite resins with improved properties containing molecules capable of being bonded to dentin were developed so that may kinds of self-curing resin cements have been produced on a commercial scale.

Resin cements generally have excellent physical properties such as high compressive strength, tensile strength and low wear resistance, and are utilized primarily as an adhesive for aesthetic appliances, especially ceramic veneers and ceramic crowns, where water soluble cements cannot be utilized because they have high water adsorption so that after being bonded they are swelled by the adsorption and finally broken. Further, resin cements of various colors have been increasingly used to provide aesthetic properties.

However, there is still a need for the development of dental self-curing resin cement compositions having enhanced physical and mechanical properties and biocompatibility.

SUMMARY OF THE INVENTION

It is an object of the invention to provide dental self-curing resin cement compositions having enhanced physical and mechanical properties and biocompatibility.

The present inventors have conducted extensive research to attain such object. As a result, the inventors found that a dental self-curing resin cement composition having enhanced physical and mechanical properties and biocompatibility can be obtained if, in addition to Bis-GMA, which has been most frequently used as a prepolymer of conventional resin cement, at least one multifunctional prepolymer formed by substituting hydrogen atoms in the hydroxyl group with methacrylate groups in Bis-BMA is used as a base prepolymer of a resin cement composition along with a diluent, an inorganic filler, an adhesive monomer, a polymerization initiator and other additives in proper quantities.

In particular, the inventors have found that the multifunctional prepolymers formed by substituting said hydrogen atoms with said methacrylate groups in Bis-GMA have low polymerization shrinkage due to their high molecular weight, and have a higher probability to participate in a crosslinking reaction as compared with bifunctional metacrylate (Bis-BMA) due to having one or two metacrylate groups instead of a hydrophilic group, i.e., a hydroxyl group. Further, even though the unreacted prepolymers have been present after their application, it is less likely that said unreacted prepolymers flow out due to their high molecular weight. Therefore, if the prepolymers are used as a base prepolymer of resin cement compositions, resin cements with reduced water adsorption and solubility may be obtained. A large amount of inorganic fillers may also be mixed due to a decrease in viscosity caused by a decreased number of sites capable of forming a hydrogen bond.

DETAILED DESCRIPTION OF THE PRESENT INVENTION

The present invention is described in detail below.

The dental self-curing resin cement compositions according to the present invention are an ointment-ointment system and consist of (i) a Paste A composition containing 1 to 25 wt % of the multifunctional prepolymer mixture selected from a group consisting of a mixture of 2,2-bis-[4-(2-hydroxy-3-methacryloxypropoxy)phenyl]propane ("Bis-GMA") of formula 1 with trifunctional methacrylate (Tri-GMA) of formula 2, a mixture of Bis-GMA with tetrafunctional methacrylate (Tetra-GMA) of formula 3 and a mixture of Bis-GMA, Tri-GMA and Tetra-GMA, and further containing 1 to 20 wt % of a diluent, 0.1 to 15 wt % of an adhesive monomer, 0.1 to 3 wt % of a polymerization initiator, 0.1 to 3 wt % of a polymerization inhibitor, 0.1 to 2 wt % of a light stabilizer, 0.1 to 2 wt % of an antioxidant, 0.005 to 1 wt % of an inorganic pigment and some inorganic filler, wherein the sum of wt % of all the components is 100 wt %; and ii) a Paste B composition containing 1 to 25 wt % of the same prepolymer mixture in the Paste A composition, and further containing 1 to 20 wt % of a diluent, 0.1 to 15 wt % of an adhesive monomer, 0.1 to 3 wt % of a reductant, 0.1 to 3 wt % of a polymerization inhibitor, 0.1 to 2 wt % of a light stabilizer, 0.1 to 2 wt % of an antioxidant, 0.005 to 1 wt % of an inorganic pigment and some inorganic filler, wherein the sum of wt % of all the components is 100 wt %.

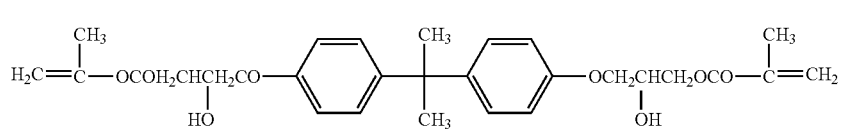

[Formula 1]

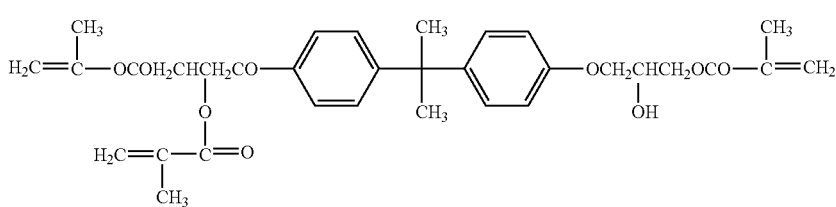

[Formula 2]

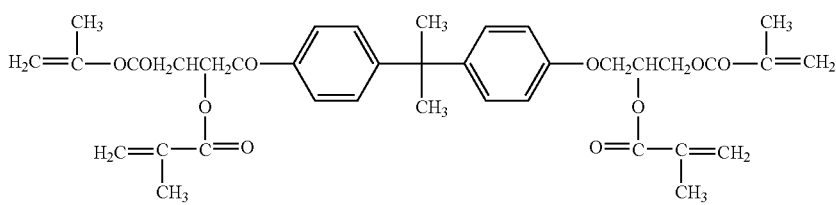

[Formula 3]

In accordance with scheme 1 below, Tri-GMA of formula 2 and Tetra-GMA of formula 3, constituting the prepolymer mixture used as a base prepolymer in the dental self-curing resin cement compositions of the invention, may be synthesized by substituting at least one hydrogen atom in the two hydroxyl groups with the methacrylate group in the Bis-GMA molecule of formula 1. That is, scheme 1 shows that Tri-GMA and Tetra-GMA may be quantitatively synthesized by reacting Bis-GMA with methacryloyl chloride in the presence of an organic amine, for example, triethylamine. The resulting multifunctional prepolymer mixture can be separated into Bis-GMA, Tri-GMA and Tetra-GMA by passing though a column eluted with a mixture of ethyl acetate and n-hexane (1:1 volume ratio). The respective prepolymers thus separated can be mixed again in the ratio according to the present invention. Also, the prepolymer mixture containing Bis-GMA, Tri-GMA and Tetra-GMA in a specific ratio can be obtained by controlling the reaction condition and the feeding ratio of methacryloyl chloride and Bis-GMA and can be directly used in the present invention without a specific separation process.

[Scheme 1]

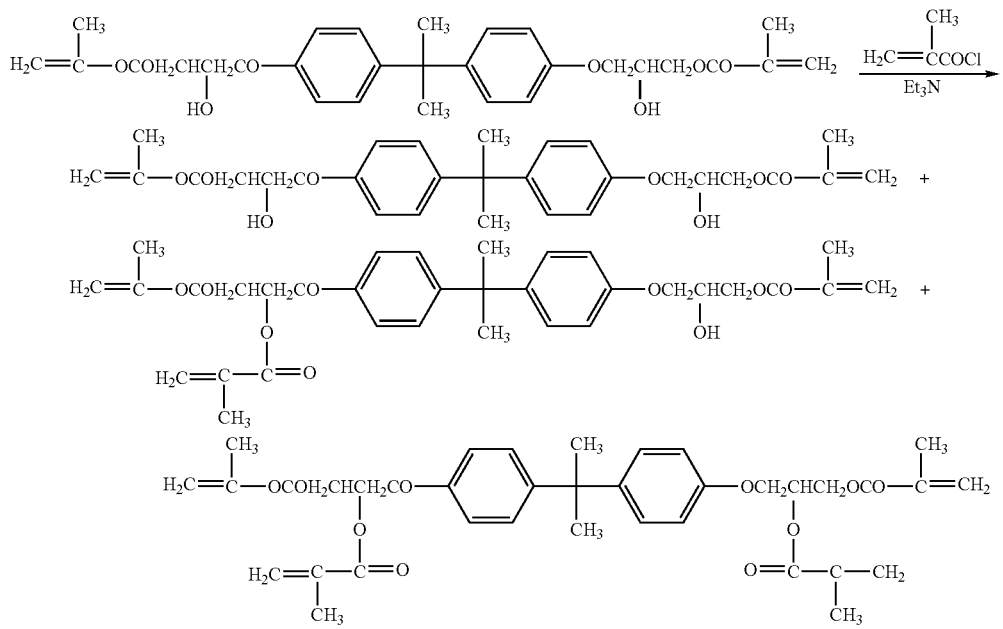

Such a prepolymer mixture may constitute an amount of 1 to 25 wt % of the total weight of the Paste A or B composition in the Paste A or B composition of the dental self-curing resin cement compositions.

The prepolymer mixture to be used may be a mixture of Bis-GMA and Tri-GMA, a mixture of Bis-GMA and Tetra-GMA or a mixture of Bis-GMA, Tri-GMA and Tetra-GMA. The mixture of Bis-GMA and Tri-GMA consists of 95~5 wt % of Bis-GMA and 5~95 wt % of Tri-GMA. The mixture of Bis-GMA and Tetra-GMA consists of 95~5 wt % of Bis-GMA and 5~95 wt % of Tetra-GMA. The mixture of Bis-GMA, Tri-GMA and Tetra-GMA consists of 90~5 wt % of Bis-GMA, 90~5 wt % of Tri-GMA and 90~5 wt % of Tetra-GMA.

In accordance with the present invention, the Paste A and B compositions comprise a diluent to reduce the viscosity of the prepolymer mixture. Suitable examples of the diluent include methyl methacrylate, ethylene glycol dimethacrylate (EGDMA), diethylene glycol dimethacrylate (DEGDMA), triethylene glycol dimethacrylate (TEGDMA), 1,4-butane diol dimethacrylate, 1,6-hexane diol dimethacrylate, 1-methyl-1,3-propane diol dimethacrylate, etc. The diluent is comprised in an amount of 1 to 20 wt % of the total weight of the respective compositions.

In accordance with the present invention, the Paste A and B compositions comprise an inorganic filler to improve the mechanical property of the resin cement and also impart impermeability to x-ray to the resin cement. Suitable examples of the inorganic filler include quartz having a particle size of 0.005 to 20 µm, which is surface-treated with a silane coupling agent, barium glass, barium glass/silica, barium glass mixture, quartz/barium glass, silica, zirconia/silica, silica mixture, aluminosilicate, lithium aluminosilicate, barium aluminosilicate, etc. The inorganic filler is comprised in an amount of 40 to 85 wt % of the total weight of the respective compositions.

Silane-type coupling agents are primarily used for treating the surface of the inorganic filler. Representative examples of the coupling agent include gamma-methacryloxy propyltrimethoxy silane (¥-MPS), vinyl triethoxy silane, dimethyl dichlorosilane, hexamethylene disilazane, dimethyl polysiloxanze, etc.

In accordance with the present invention, the Paste A and B compositions comprise an adhesive monomer to enhance the adhesion strength of the resin cement on both teeth and a dental restoration metal. Examples of the adhesive monomer include methacrylic acid, maleic acid, p-vinylbenzoic acid, 11-methacryloxy-1,1-undecane dicarboxylic acid (MAC-10), 1,4-dimethacryloxyethylpyromellitic acid, 6-methacryloxyethyl naphthalene-1,2,6-tricarboxylic acid, 4-methacryloxymethyltrimellitic acid and its anhydride, 4-methacryloxyethyltrimellitic acid (4-MET) and its anhydride (4-META), 4-methacryloxybutyltrimellitic acid and its anhydride, 4-(2-hydroxy-3-methacryloxy)butyltrimellitic acid and its anhydride, 2,3-bis(3,4-dicarboxybenzoyloxy) propylmethacrylate, 2-, 3- or 4-methacryloxybenzoic acid, N-o-dimethacryloxytyrosine, o-methacryloxytyrosine, N-methacryloxytyrosine, N-methacryloxyphenylalanine, N-methacryloyl-p-aminobenzoic acid, N-methacryloyl-o-aminobenzoic acid, an addition product of glycidylmethacrylate with N-phenylglycine or N-tolylglycine, 4-[(2-hydroxy-3-methacryloxypropyl)amino]phthalic acid, 3- or 4-[N-methyl-N-(2-hydroxy-3-methacryloxy)amino]phthalic acid, methacryloylaminosalicylic acid and methacryloxy salicylic acid, an addition product of 1 mole 3,3,4,4'-benzophenone tetracarboxylic acid anhydride (BTDA) or 3,3,4,4-biphenyltetracarboxylic acid dianhydride and 2-(3,4-dicarboxylbenzoyloxy)-1,3-dimethacryloxypropane, 2-methacryloxyethyl acid phosphate, 2- and 3-methacryloxypropyl acid phosphate, 4-methacryloxybutyl acid phosphate, 6-methacryloxybutyl acid phosphate, 8-methacryloxybutyl acid phosphate, 10-methacryloxybutyl acid phosphate, 12-methacryloxybutyl acid phosphate, bis(2-methacryloxyethyl) acid phosphate, 2-methacryloxyethylphenyl acid phosphate, 2-methacryloxyethyl p-methoxyphenyl acid phosphate, 2-sulfoethylmethacrylate, 2- or 1-sulfo-1 or 2-propylmethacrylate, 1- or 3-sulfo-2-butyl methacrylate, 3-bromo-2-sulfo-2-propylmethacrylate, 3-methoxy-1-sulfo-2-propylmethacrylate, 1,1-dimethyl-2-sulfoethylmethacrylamide propane sulfonic acid, 2-methyl-2-methacrylamide propylsulfonic acid, etc. The adhesive monomer is comprised in an amount of 0.1 to 15 wt % of the total weight of the respective compositions.

In the dental self-curing resin cement composition according to the present invention, free radicals are generated when a polymerization initiator and a reductant are mixed with each other, and said free radicals initiate the polymerization reaction to result in curing the resin cement composition. The polymerization reaction is primarily initiated by both a polymerization initiator and an amine-type reductant. The initiator used is benzoyl peroxide (BPO) or azobisisobutyronitrile (AIBN) and is added in an amount of 0.1 to 3 wt % of the total weight of the Paste A composition. The reductant used, which practically initiates the polymerization reaction when the hydrogen of the reductant is extracted by the initiator, is N,N-dihydroxymethyl-p-toluidine or N,N-dihydroxyethyl-p-toluidine and is added in an amount of 0.1 to 3 wt % of the total weight of the Paste B composition.

Other additives, such as a polymerization inhibitor, a light stabilizer, an antioxidant, and an inorganic pigment used for providing color to the resin cement, may be added. A polymerization inhibitor such as hyroquinone (HQ), hydroquinone monomethyl ether or hydroquinone monoethyl ether may be added in an amount of 0.01 to 3 wt % of the total weight of the Paste A or B composition. A light stabilizer such as bis(2,2,6,6-tetramethyl-4-piperidinyl)sebacate, octyl-p-methoxycinnamate, 2,4-dihydroxybenzophenone, 2-hydroxy-4-methoxybenzopheione, disodium-2,2-dihydroxy-4,4-dimethoxybenzophenone-5,5-disulfonate and Tinuvin may be added in an amount of 0.01 to 2 wt % of the total weight of the Paste A or B composition. An antioxidant such as N-octadecyl-3-(3,5-ditetrabutyl-4-hydroxyphenyl)propionate, cyclic neopentaneterayl bis(octadecyl phosphate), 4,4-butylidine bis(3-methyl-6-tetrabutylphenyl-di-tridecyl)phosphite, tri(2,4-ditetrabutylphenyl) phosphite, 2,6-ditertiarybutyl-4-methylphenol butylated hydroxy toluene (BHT) may be added in an amount of 0.01 to 3 wt % of the total weight of the Paste A or B composition. An inorganic pigment such as iron oxide and titanium dioxide inorganic pigment may be added in an amount of 0.005 to 1 wt % of the total weight of the Paste A or B composition.

Mixing and degassing are availably conducted by using a vacuum mixer in the process for preparing the dental self-curing resin cement according the present invention.

The physical properties of the prepared dental self-curing resin cement compositions are estimated as follows:

1) Polymerization Shrinkage

A cylindrical specimen of the dental resin cement composition [6.0 cm (diameter)×3.3 mm (height)] is put into a mold, and then cured. A density (d) of the specimen before and after curing is measured by using a picnometer and calculated according to the following formula:

$$\text{Polymerization shrinkage (\%)} = (1 - d_{uncured}/d_{cured}) \times 100$$

2) Water Absorption and Water Solubility

A dental resin cement composition is made into about a 6 cm (diameter)×3 mm (thickness) specimen, which is cured. The weight of the cured specimen is measured, and the specimen is then dipped into distilled water at 37° C. Every 24 or 48 hours, the specimen is taken out, water is removed from surface of the specimen, and the weight of the specimen is measured. Moisture absorption is calculated by the following formula:

Water absorption (%)=[(weight after dipping−weight before dipping)/weight before dipping]×100

Water solubility is measured by taking out the specimen and removing water from it. The specimen is again completely dried in a desiccator to have uniform weight, and the weight of the specimen is measured. Water solubility is calculated by the following formula:

Water Solubility (%)=[(weight before dipping−weight after dipping and complete drying)/weight before dipping]×100

3) Film Thickness

Two (2) glass plates having a thickness of 5 mm or more and a contact area of 200±5 mm$^2$ are placed on a device for measuring the film thickness. Then, their overall thickness (A) is measured within a margin of error of ±1.25 μm. The top plate is removed and a mixed resin cement of 0.1±0.05 ml is placed on the center of the bottom plate to position the resin cement below a front wall of the device, and the top plate is placed back again. A load of 150±N is applied to the plates at 10 seconds before the end of operation and overall thickness (B) is measured as suggested by a manufacturer. The difference of A and B is reported as the film thickness.

4) Curing Time

A metal mold is placed under conditions of 23±1° C. Aluminum foil is then laid on the mold, and a specimen of mixed resin cement is filled horizontally into the mold. After 60 sec of mixing the resin cement, the lower part of a marker is carefully placed vertically on the surface of the cement for 5 sec. Marking by means of the marker is repeatedly conducted at 30 sec intervals until a complete round mark is not formed on the surface of the cement by the marker when the surface of the resin cement is observed at 2 times magnification to determine approximate curing time. After determining the approximate curing time, the test for measuring curing time as described above is conducted at 30 sec before the approximate curing time and at 10 sec intervals. The time from the mixing time to the time formed complete round mark on the surface of the cement is reported. The above procedure repeats three times to report the average of the results as curing time.

5) Compressive Strength

A device for measuring the compressive strength is operated at a crosshead rate of 0.75±0.30 mm/min.

After mixing the resin cement, the mixed resin cement is filled into a dividable frame within 60 sec until it overflows. A frame and a cramp used to prepare a specimen are placed under some pressure from a bottom plate. The resin cement formed into a mass is taken out of the frame, and a top plate is pressed onto the frame. The frame and the plate are placed into a screw clamp to join firmly. After mixing the resin cement, overall constructions transfer into a cabinet within 120 sec. At 1 hr after the mixing, the plate is removed and the surface of the specimen is polished to position the vertical section of the specimen vertically in respect to its long axis. The polisher to be used should not be coarse. In this regard, the surface of the specimen is more easily polished with wet silicon carbide paper (400 grade). Once the surface has been polished, the specimen is removed from the frame and the surface is examined with the naked eye without using a microscope in respect to the existence of broken edges and pores caused by air. Five (5) samples are prepared. Once the samples are prepared, they are immersed in grade 3 water according to the international standard. The respective diameters of the five samples are measured 2 times within an accuracy of ±0.01 mm, and the respective averages of the obtained values are regarded to be the respective diameters thereof.

At 24 hrs after the mixing, a sample whose edge is trimmed flatly is placed between press plates of the device for measuring physical properties, and a compressive load is applied along the long axis of the sample. The load is reported when the sample is broken, and the compressive strength is calculated by the following formula:

$$C=4\rho/(\pi \times d^2)$$

Wherein ρ refers to a maximum load (N), and d is a diameter (mm) of the sample.

6) Adhesion Strength

A tooth specimen or a metal is cut in parallel with an occlusal surface using a microtome for uniform thickness. Then, a tube containing the resin cement is attached thereto to determine adhesion strength using Instron.

The present invention is illustrated in detail by the examples below. However, the examples presented here are for illustrative purposes only and should not be construed to limit the invention.

EXAMPLE 1

To prepare a self-curing resin cement composition, 10 wt % of a prepolymer mixture consisting of 45 wt % of Bis-GMA, 45 wt % of Tri-GMA and 10 wt % of Tetra-GMA; 5 wt % of TEGDMA; 5 wt % of 4-META; 1.0 wt % of BPO; 0.5 wt % of HQ; 0.5 wt % of Tinuvin; 0.5 wt % of BHT; 0.01 wt % of iron oxide and 77.49 wt % of silica gel were mixed to prepare a Paste A composition. 10 wt % of a prepolymer mixture consisting of 45 wt % of Bis-GMA, 45 wt % of Tri-GMA and 10 wt % of Tetra-GMA; 5 wt % of TEGDMA; 5 wt % of 4-META; 1.0 wt % of N,N-dihydroxymethyl-p-toluidine; 0.5 wt % of HQ; 0.5 wt % of Tinuvin; 0.5 wt % of BHT; 0.01 wt % of iron oxide and 77.49 wt % of silica gel were mixed to prepare a Paste B composition.

EXAMPLE 2

A self-curing resin cement composition was prepared in the same manner set forth in Example 1, except that 10 wt % of a prepolymer mixture consisting of 50 wt % of Bis-GMA and 50 wt % of Tri-GMA was used as a prepolymer of the Paste A and B compositions.

EXAMPLE 3

A self-curing resin cement composition was prepared in the same manner set forth in Example 1, except that 10 wt % of a prepolymer mixture consisting of 50 wt % of Bis-GMA and 50 wt % of Tetra-GMA was used as a prepolymer of the Paste A and B compositions.

COMPARATIVE EXAMPLE 1

A self-curing resin cement composition was prepared in the same manner set forth in Example 1, except that 10 wt % of Bis-GMA was used as a prepolymer of the Paste A and B compositions.

COMPARATIVE EXAMPLE 2

A self-curing resin cement composition was prepared in the same manner set forth in Example 1, except that 10 wt % of Tri-GMA was used as a prepolymer of the Paste A and B compositions.

COMPARATIVE EXAMPLE 3

A self-curing resin cement composition was prepared in the same manner set forth in Example 1, except that 10 wt % of Tetra-GMA was used as a prepolymer of the Paste A and B compositions.

The self-curing resin cement compositions prepared in the above Examples and Comparative Examples are measured on mechanical and physical properties. The results are shown in Table 1 below.

TABLE 3

|  | Example | | | Comparative Example | | |
| --- | --- | --- | --- | --- | --- | --- |
|  | 1 | 2 | 3 | 1 | 2 | 3 |
| Polymerization Shrinkage (%) | 5.5 | 6.1 | 5.9 | 6.3 | 5.7 | 5.3 |
| Water absorption (%) | 13 | 31 | 12 | 37 | 11 | 10 |
| Water solubility (%) | 1.5 | 2.3 | 1.0 | 4.3 | 1.3 | 1.1 |
| Curing time (sec) | 180 | 179 | 182 | 177 | 180 | 183 |
| Film thickness (μm) | 12 | 13 | 14 | 12 | 13 | 14 |
| Compressive strength (MPa) | 310 | 301 | 291 | 274 | 301 | 309 |
| Adhesion strength (MPa) (tooth-resin cement) | 31 | 28 | 26 | 31 | 24 | 21 |
| Adhesion strength (MPa) (metal-resin cement) | 34 | 31 | 29 | 35 | 29 | 28 |

As shown in Table 1, the compositions according to the present invention (Examples 1, 2 and 3) have excellent physical and mechanical properties, such as polymerization shrinkage and water absorption, while the compositions not according to the present invention (Comparative Examples 1, 2 and 3) have poor polymerization shrinkage and water absorption or low adhesion strength.

While the present invention has been shown and described with particular examples, it will be apparent to those skilled in the art that many changes and modifications can be made without departing from the spirit and scope of the invention as defined in the appended claims.

What is claimed is:

1. A dental self-curing resin cement composition of an ointment-ointment system comprising:
   i) a Paste A composition containing 1 to 25 wt % of the multifunctional prepolymer mixture selected from a group consisting of a mixture of 95 to 5 wt % of 2,2-bis-[4-(2-hydroxy-3-methacryloxypropoxy)phenyl]propane ("Bis-GMA") of formula 1 and 5 to 95 wt % of trifunctional methacrylate (Tri-GMA) of formula 2 based on the weight of the prepolymer mixture, a mixture of 95 to 5 wt % of Bis-GMA and 5 to 95 wt % of tetrafunctional methacrylate (Tetra-UMA) of formula 3 based on the weight of the prepolymer mixture, and a mixture of 90 to 5 wt % of Bis-GMA, 90 to 5 wt % of Tri-GMA and 90 to 5 wt % of Tetra-GMA based on the weight of the prepolymer mixture; 1 to 20 wt % of a diluent; 0.1 to 15 wt % of an adhesive monomer; 0.1 to 3 wt % of a polymerization initiator; 0.1 to 3 wt % of a polymerization inhibitor; 0.1 to 2 wt % of a light stabilizer; 0.1 to 2 wt % of an antioxidant; 0.005 to 1 wt % of an inorganic pigment and some inorganic filler, wherein the sum of wt % of all components is 100 wt %; and
   ii) a Paste B composition containing 1 to 25 wt % of the same prepolymer mixture in the Paste A composition; 1 to 20 wt % of a diluent; 0.1 to 15 wt % of an adhesive monomer; 0.1 to 3 wt % of a reductant; 0.1 to 3 wt % of a polymerization inhibitor; 0.1 to 2 wt % of a light stabilizer; 0.1 to 2 wt % of an antioxidant; 0.005 to 1 wt % of an inorganic pigment and some inorganic filler, wherein the sum of wt % of all components is 100 wt %

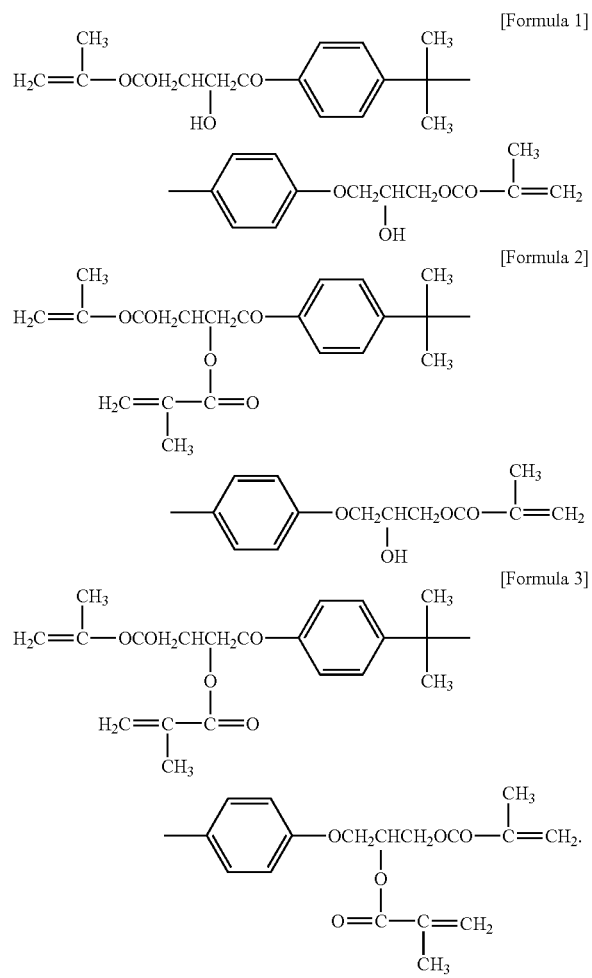

2. The dental self-curing resin cement composition according to claim 1, wherein the diluent is selected from a group consisting of methyl methacrylate, ethylene glycol dimethacrylate, diethylene glycol dimethacrylate, triethylene glycol dimethacrylate, 1,4-butane diol dimethacrylate, 1,6-hexane diol dimethacrylate, 1-methyl-1,3-propane diol dimethacrylate and mixtures thereof.

3. The dental self-curing resin cement composition according to claim 1, wherein the adhesive monomer is selected from a group consisting of methacrylic acid, maleic acid, p-vinylbenzoic acid, 11-methacryloxy-1,1-undecane dicarboxylic acid (MAC-10), 1,4-dimethacryloxyethylpyromellitic acid, 6-methacryloxyethyl naphthalene-1,2,6-tricarboxylic acid, 4-methacryloxymethyltrimellitic acid and its anhydride, 4-methacryloxyethyltrimellitic acid (4-MET) and its anhydride (4-META), 4-methacryloxybutyltrimellitic acid and its anhydride, 4-(2-hydroxy-3-methacryloxy) butyltrimellitic acid and its anhydride, 2,3-bis(3,4-dicarboxybenzoyloxy)propylmethacrylate, 2-, 3- or 4-methacryloxybenzoic acid, N-o-dimethacryloxytyrosine, o-methacryloxytyrosine, N-methacryloxytyrosine, N-methacryloxyphenylalanine, N-methacryloyl-p-aminobenzoic acid, N-methacryloyl-o-aminobenzoic acid, an addition product of glycidylmethacrylate with N-phenylglycine or N-tolylglycine, 4-[(2-hydroxy-3-methacryloxypropyl) amino]phthalic acid, 3- or 4-[N-methyl-N-(2-hydroxy-3-methacryloxy)amino]phthalic acid, methacryloylaminosalicylic acid and methacryloxy salicylic acid, an addition product of 1 mole 3,3,4,4'-benzophenone tetracarboxylic acid anhydride (BTDA) or 3,3,4,4-biphenyltetracarboxylic acid dianhydride and 2-(3,4-dicarboxylbenzoyloxy)-1,3-dimethacryloxypropane, 2-methacryloxyethyl acid phosphate, 2- and 3-methacryloxypropyl acid phosphate, 4-methacryloxybutyl acid phosphate, 6-methacryloxybutyl acid phosphate, 8-methacryloxybutyl acid phosphate, 10-methacryloxybutyl acid phosphate, 12-methacryloxybutyl acid phosphate, bis(2-methacryloxyethyl) acid phosphate, 2-methacryloxyethylphenyl acid phosphate, 2-methacryloxyethyl p-methoxyphenyl acid phosphate, 2-sulfoethylmethacrylate, 2- or 1-sulfo-1 or 2-propyhnethacrylate, 1- or 3-sulfo-2-butyl methacrylate, 3-bromo-2-sulfo-2-propylmethacrylate, 3-methoxy-1-sulfo-2-propylmethacrylate, 1,1-dimethyl-2-sulfoethylmethacrylamide propane sulfonic acid and 2-methyl-2-methacrylamide propylsulfonic acid and mixtures thereof.

4. The dental self-curing resin cement composition according to claim 1, wherein the polymerization initiator is selected from a group consisting of benzoyl peroxide (BPO), azobisisobutyronitrile (AIBN) and a mixture thereof.

5. The dental self-curing resin cement composition according to claim 1, wherein the reductant is selected from a group consisting of N,N-dihydroxymethyl-p-toluidine, N,N-dihydroxyethyl-p-toluidine and a mixture thereof.

6. The dental self-curing resin cement composition according to claim 1, wherein the polymerization inhibitor is selected from a group consisting of hyroquinone, hydroquinone monomethyl ether, hydroquinone monoethyl ether and mixtures thereof.

7. The dental self-curing resin cement composition according to claim 1, wherein the light stabilizer is selected from a group consisting of bis(2,2,6,6-tetramethyl-4-piperidinyl)sebacate, octyl-p-methoxycinnamate, 2,4-dihydroxybenzophenone, 2-hydroxy-4-methoxybenzophenone, disodium-2,2-dihydroxy-4,4-dimethoxybenzophenone-5,5-disulfonate, 2-(2H-benzotriazol-2-yl)-p-cresol and mixtures thereof.

8. The dental self-curing resin cement composition according to claim 1, wherein the antioxidant is selected from a group consisting of N-octadecyl-3-(3,5-ditetrabutyl-4-hydroxyphenyl)propionate, cyclic neopentaneterayl bis (octadecyl phosphate), 4,4-butylidine bis(3-methyl-6-tetrabutylphenyl-di-tridecyl)phosphite, tri(2,4-ditetrabutylphenyl)phosphite, 2,6-ditertiarybutyl-4-methylphenol butylated hydroxy toluene and mixtures thereof.

9. The dental self-curing resin cement composition according to claim 1, wherein the inorganic pigment is selected from a group consisting of iron oxide, titanium dioxide and a mixture thereof.

* * * * *